United States Patent
Bowling et al.

(10) Patent No.: US 10,743,952 B2
(45) Date of Patent: Aug. 18, 2020

(54) SYSTEM AND METHOD FOR MANIPULATING AN ANATOMY

(71) Applicant: MAKO Surgical Corp., Ft. Lauderdale, FL (US)

(72) Inventors: David Gene Bowling, Los Ranchos de Albuquerque, NM (US); John Michael Stuart, Rio Rancho, NM (US); Jerry A. Culp, Kalamazoo, MI (US); Donald W. Malackowski, Schoolcraft, MI (US); Jose Luis Moctezuma de la Barrera, Freiburg (DE); Patrick Roessler, Merzhausen (DE); Joel N. Beer, Albuquerque, NM (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 123 days.

(21) Appl. No.: 16/130,089

(22) Filed: Sep. 13, 2018

(65) Prior Publication Data
US 2019/0008596 A1 Jan. 10, 2019

Related U.S. Application Data

(63) Continuation of application No. 15/157,833, filed on May 18, 2016, now Pat. No. 10,098,704.
(Continued)

(51) Int. Cl.
*B25J 9/02* (2006.01)
*A61B 34/30* (2016.01)
(Continued)

(52) U.S. Cl.
CPC .......... *A61B 34/30* (2016.02); *A61B 17/1675* (2013.01); *A61B 34/10* (2016.02);
(Continued)

(58) Field of Classification Search
CPC . A61B 19/2203; A61B 34/30; A61B 17/1675; A61B 17/1695;
(Continued)

(56) References Cited

U.S. PATENT DOCUMENTS

| 6,128,547 | A | 10/2000 | Tomoeda et al. |
| 7,747,311 | B2 | 6/2010 | Quaid, III |

(Continued)

FOREIGN PATENT DOCUMENTS

JP H10166242 A 6/1998

OTHER PUBLICATIONS

International Search Report for PCT/US2016/033062; dated Aug. 16, 2016; 13 pages.
(Continued)

*Primary Examiner* — Dalena Tran
(74) *Attorney, Agent, or Firm* — Howard & Howard Attorneys PLLC

(57) ABSTRACT

A system includes a robotic manipulator comprising an arm and an end effector coupled to the arm and being moveable by the arm for interacting with a target site in a manual mode and an autonomous mode of operation. A navigation system is configured to track a position of the end effector and the target site. One or more controllers are configured to define a first virtual boundary relative to the target site, prevent the end effector from penetrating the first virtual boundary in the manual mode, and allow the end effector to penetrate the first virtual boundary in the autonomous mode.

20 Claims, 8 Drawing Sheets

Related U.S. Application Data

(60) Provisional application No. 62/163,672, filed on May 19, 2015.

(51) Int. Cl.
| | | |
|---|---|---|
| *A61B 34/32* | (2016.01) | |
| *A61B 34/00* | (2016.01) | |
| *A61B 34/20* | (2016.01) | |
| *A61B 34/10* | (2016.01) | |
| *A61B 34/37* | (2016.01) | |
| *A61B 90/00* | (2016.01) | |
| *A61B 17/16* | (2006.01) | |
| *A61B 18/00* | (2006.01) | |

(52) U.S. Cl.
CPC .............. *A61B 34/20* (2016.02); *A61B 34/32* (2016.02); *A61B 34/37* (2016.02); *A61B 34/76* (2016.02); *A61B 90/39* (2016.02); *A61B 2018/00565* (2013.01); *A61B 2018/00601* (2013.01); *A61B 2034/105* (2016.02); *A61B 2034/107* (2016.02); *A61B 2034/2055* (2016.02); *A61B 2034/2059* (2016.02); *A61B 2034/2068* (2016.02); *A61B 2090/3937* (2016.02); *A61B 2090/3975* (2016.02)

(58) Field of Classification Search
CPC . A61B 2018/00565; A61B 2018/00601; Y10S 901/09; Y10S 901/47; B25J 9/1628; B25J 9/1666; G05B 2219/40415; G05B 2219/45117
USPC .......... 700/245, 258; 901/2, 41, 47; 606/130
See application file for complete search history.

(56) References Cited

U.S. PATENT DOCUMENTS

| | | |
|---|---|---|
| 7,815,644 B2 | 10/2010 | Masini |
| 8,287,522 B2 | 10/2012 | Moses et al. |
| 9,008,757 B2 | 4/2015 | Wu |
| 9,119,655 B2 | 9/2015 | Bowling et al. |
| 9,381,085 B2 | 7/2016 | Axelson, Jr. et al. |
| 9,427,334 B2 | 8/2016 | Axelson, Jr. et al. |
| 9,603,665 B2 | 3/2017 | Bowling et al. |
| 10,098,704 B2 | 10/2018 | Bowling et al. |
| 2003/0109780 A1* | 6/2003 | Coste-Maniere ...... B25J 9/1671 600/407 |
| 2004/0128026 A1* | 7/2004 | Harris ................... B25J 9/1689 700/245 |
| 2005/0228440 A1* | 10/2005 | Brock .................... A61B 34/71 606/205 |
| 2008/0077158 A1 | 3/2008 | Haider et al. |
| 2008/0281343 A1 | 11/2008 | Dewey et al. |
| 2012/0330429 A1 | 12/2012 | Axelson, Jr. et al. |
| 2013/0006267 A1 | 1/2013 | Odermatt et al. |
| 2013/0038707 A1 | 2/2013 | Cunningham et al. |
| 2013/0060278 A1 | 3/2013 | Bozung et al. |
| 2013/0169423 A1 | 7/2013 | Iorgulescu et al. |
| 2014/0039681 A1 | 2/2014 | Bowling et al. |
| 2014/0180290 A1 | 6/2014 | Otto et al. |
| 2014/0257293 A1 | 9/2014 | Axelson, Jr. et al. |
| 2014/0276943 A1 | 9/2014 | Bowling et al. |
| 2014/0276949 A1 | 9/2014 | Staunton et al. |

OTHER PUBLICATIONS

English language abstract for JPH 10-166242 extracted from espacenet.com database on Mar. 11, 2020, 2 pages.

* cited by examiner

SYSTEM AND METHOD FOR MANIPULATING AN ANATOMY

CROSS-REFERENCE TO RELATED APPLICATION

This application is a continuation of U.S. patent application Ser. No. 15/157,833, filed May 18, 2016, which claims priority to and the benefit of U.S. provisional patent application No. 62/163,672, filed May 19, 2015, the disclosures of which are hereby incorporated by reference in their entirety.

TECHNICAL FIELD

The present invention relates generally to a system and method for manipulating an anatomy with a tool of a surgical system, and more specifically, constraining the tool using virtual boundaries.

BACKGROUND

Recently, operators have found it useful to use robotic devices to assist in the performance of surgical procedures. A robotic device typically includes a moveable arm having a free, distal end, which may be placed with a high degree of accuracy. A tool that is applied to the surgical site attaches to the free end of the arm. The operator is able to move the arm and thereby precisely position the tool at the surgical site to perform the procedure.

In robotic surgery, virtual boundaries are created prior to surgery using computer aided design software to delineate areas in which the tool may maneuver from areas in which the tool is restricted. For instance, in orthopedic surgery a virtual cutting boundary may be created to delineate sections of bone to be removed by the tool during the surgery from sections of bone that are to remain after the surgery.

A navigation system tracks movement of the tool to determine a position and/or orientation of the tool relative to the virtual boundary. The robotic system cooperates with the navigation system to guide movement of the tool so that the tool does not move beyond the virtual boundary. Virtual boundaries are often created in a model of a patient's bone and fixed with respect to the bone so that when the model is loaded into the navigation system, the navigation system may track movement of the virtual boundary by tracking movement of the bone.

Operators often desire dynamic control of the tool in different cutting modes during a surgical operation. For example, in some instances, the operator may desire a manual mode to control the tool manually for bulk cutting of the anatomy. In other instances, the operator may desire to control the tool in an autonomous mode for automated and highly accurate cutting of the anatomy. In conventional systems, a virtual boundary associated with a target surface of the anatomy remains active regardless of the mode of control. In other words, the same virtual boundary is on whether the tool is controlled in the autonomous mode or manual mode, for example. The manipulator generally does not allow advancement of the tool beyond the boundary in either mode. However, in some cases, the manipulator may inadvertently allow movement of the tool beyond the boundary. For instance, in the manual mode, the operator may apply such a large amount of force on the tool that exceeds the ability of the manipulator to prevent movement of the tool beyond the boundary. In this case, cutting of the anatomy may occur beyond the virtual boundary thereby deviating from the desired target surface.

There is a need in the art for systems and methods for solving at least the aforementioned problems.

SUMMARY

One embodiment of a system is provided. The system includes a robotic manipulator comprising an arm and an end effector coupled to the arm and being moveable by the arm for interacting with a target site in a manual mode and an autonomous mode of operation. A navigation system is configured to track a position of the end effector and the target site. One or more controllers are configured to define a first virtual boundary relative to the target site, prevent the end effector from penetrating the first virtual boundary in the manual mode, and allow the end effector to penetrate the first virtual boundary in the autonomous mode.

One embodiment of a method of operating a system is provided. The system includes a robotic manipulator comprising an arm and an end effector coupled to the arm and being moveable by the arm for interacting with a target site in a manual mode and an autonomous mode of operation. A navigation system is configured to track a position of the end effector and the target site. One or more controllers are configured to perform the steps of defining a first virtual boundary relative to the target site, preventing the end effector from penetrating the first virtual boundary in the manual mode, and allowing the end effector to penetrate the first virtual boundary in the autonomous mode.

When the end effector is operated in the manual mode, and under greater influence by the operator, the system and method constrain the end effector from closely approaching the target site by using the virtual boundary. When the end effector is operated in the autonomous mode, and under less influence by the operator, the system and method advantageously provide the opportunity to enable the end effector to bypass the virtual boundary effector and approach the target site more closely. By doing so, the system and method provide increase versatility and performance of the surgical system without limiting advancement of the tool beyond the boundary in the autonomous mode.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Overview

Figure 1:
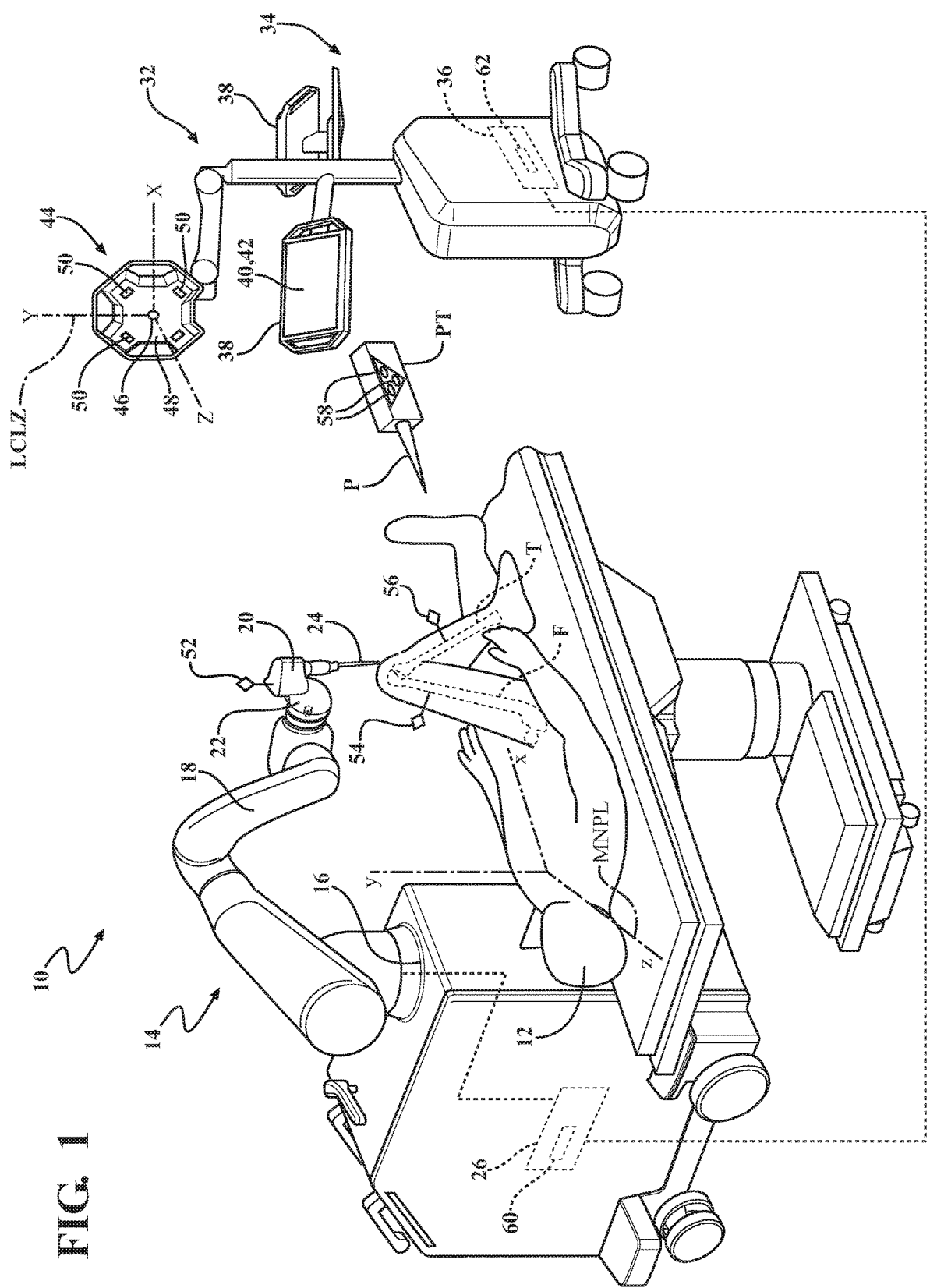
FIG. 1 is a perspective view of a system for manipulating an anatomy of a patient with a tool according to one embodiment of the invention.

Referring to the Figures, wherein like numerals indicate like or corresponding parts throughout the several views, a system 10 and method for manipulating an anatomy of a patient 12 are shown throughout. As shown in FIG. 1, the system 10 is a robotic surgical cutting system for cutting away material from the anatomy of the patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal. In other embodiments, the surgical procedure involves partial or total knee or hip replacement surgery. The system 10 is designed to cut away material to be replaced by surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation," the disclosure of which is hereby incorporated by reference. Those skilled in the art appreciate that the system and method disclosed herein may be used to perform other procedures, surgical or non-surgical, or may be used in industrial applications or other applications where robotic systems are utilized.

The system 10 includes a manipulator 14. The manipulator 14 has a base 16 and a linkage 18. The linkage 18 may comprise links forming a serial arm or parallel arm configuration. A tool 20 couples to the manipulator 14 and is movable relative to the base 16 to interact with the anatomy. The tool 20 forms part of an end effector 22 attached to the manipulator 14. The tool 20 is grasped by the operator. One exemplary arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference. The tool 20 includes an energy applicator 24 designed to contact the tissue of the patient 12 at the surgical site. The energy applicator 24 may be a drill, a saw blade, a bur, an ultrasonic vibrating tip, or the like. The manipulator 14 also houses a manipulator computer 26, or other type of control unit.

Figure 2:
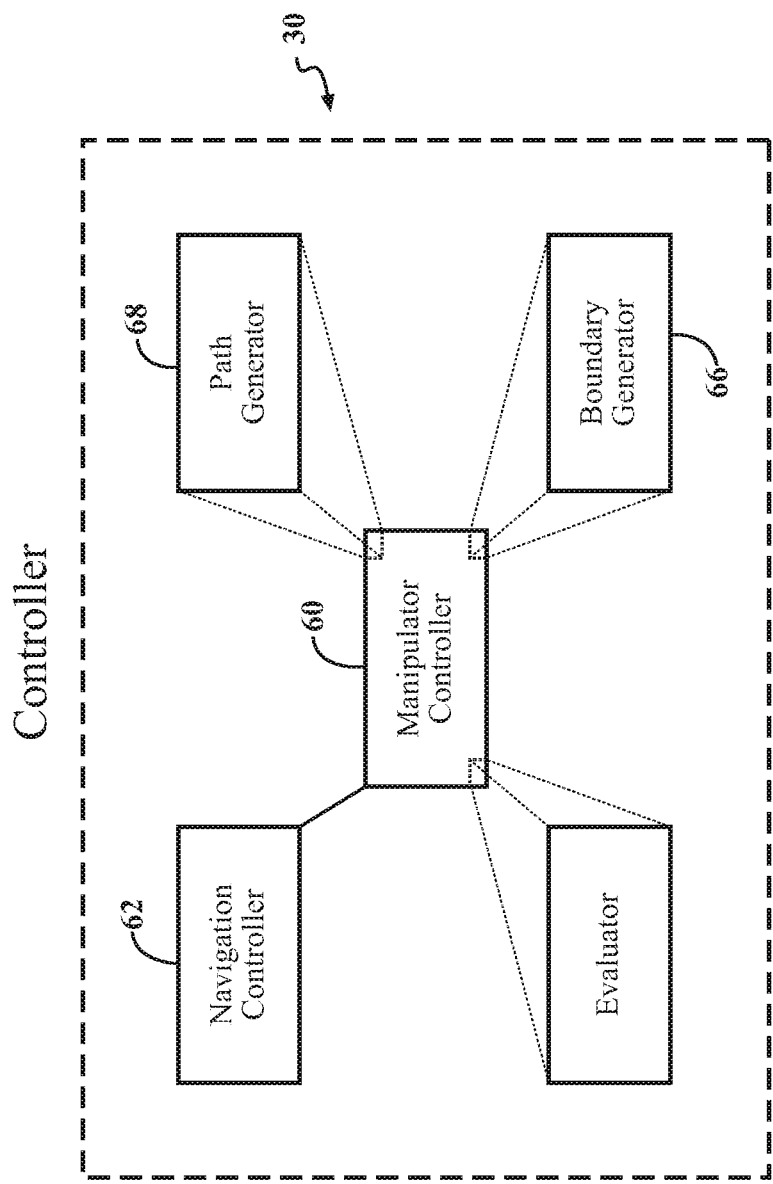
FIG. 2 is a schematic view of a controller for controlling the surgical system according to one embodiment of the invention.

Referring to FIG. 2, the system 10 includes a controller 30. The controller 30 includes software and/or hardware for controlling the manipulator 14. The controller 30 directs the motion of the manipulator 14 and controls an orientation of the tool 20 with respect to a coordinate system. In one embodiment, the coordinate system is a manipulator coordinate system MNPL (see FIG. 1). The manipulator coordinate system MNPL has an origin, and the origin is located at a point on the manipulator 14. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is set up to track movement of various objects. Such objects include, for example, the tool 20, and the anatomy, e.g., femur F and tibia T. The navigation system 32 tracks these objects to gather position information of each object in a localizer coordinate system LCLZ. Coordinates in the localizer coordinate system LCLZ may be transformed to the manipulator coordinate system MNPL using conventional transformation techniques. The navigation system 32 is also capable of displaying a virtual representation of their relative positions and orientations to the operator.

The navigation system 32 includes a computer cart assembly 34 that houses a navigation computer 36, and/or other types of control units. A navigation interface is in operative communication with the navigation computer 36. The navigation interface includes one or more displays 38. First and second input devices 40, 42 such as a keyboard and mouse may be used to input information into the navigation computer 36 or otherwise select/control certain aspects of the navigation computer 36. Other input devices 40, 42 are contemplated including a touch screen (not shown) or voice-activation. The controller 30 may be implemented on any suitable device or devices in the system 10, including, but not limited to, the manipulator computer 26, the navigation computer 36, and any combination thereof.

The navigation system 32 also includes a localizer 44 that communicates with the navigation computer 36. In one embodiment, the localizer 44 is an optical localizer and includes a camera unit 46. The camera unit 46 has an outer casing 48 that houses one or more optical position sensors 50. The system 10 includes one or more trackers. The trackers may include a pointer tracker PT, a tool tracker 52, a first patient tracker 54, and a second patient tracker 56. The trackers include active markers 58. The active markers 58 may be light emitting diodes or LEDs. In other embodiments, the trackers 52, 54, 56 may have passive markers, such as reflectors, which reflect light emitted from the camera unit 46. Those skilled in the art appreciate that the other suitable tracking systems and methods not specifically described herein may be utilized.

In the illustrated embodiment of FIG. 1, the first patient tracker 54 is firmly affixed to the femur F of the patient 12 and the second patient tracker 56 is firmly affixed to the tibia T of the patient 12. The patient trackers 54, 56 are firmly affixed to sections of bone. The tool tracker 52 is firmly attached to the tool 20. It should be appreciated that the trackers 52, 54, 56 may be fixed to their respective components in any suitable manner.

The trackers 52, 54, 56 communicate with the camera unit 46 to provide position data to the camera unit 46. The camera unit 46 provides the position data of the trackers 52, 54, 56 to the navigation computer 36. In one embodiment, the navigation computer 36 determines and communicates position data of the femur F and tibia T and position data of the tool 20 to the manipulator computer 26. Position data for the femur F, tibia T, and tool 20 may be determined by the tracker position data using conventional registration/navigation techniques. The position data includes position information corresponding to the position and/or orientation of the femur F, tibia T, tool 20 and any other objects being tracked. The position data described herein may be position data, orientation data, or a combination of position data and orientation data.

The manipulator computer 26 transforms the position data from the localizer coordinate system LCLZ into the manipulator coordinate system MNPL by determining a transformation matrix using the navigation-based data for the tool 20 and encoder-based position data for the tool 20. Encoders (not shown) located at joints of the manipulator 14 are used to determine the encoder-based position data. The manipulator computer 26 uses the encoders to calculate an encoder-based position and orientation of the tool 20 in the manipulator coordinate system MNPL. Since the position and orientation of the tool 20 are also known in the localizer coordinate system LCLZ, the transformation matrix may be generated.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include sets of instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules.

In one embodiment, the controller 30 includes a manipulator controller 60 for processing data to direct motion of the manipulator 14. The manipulator controller 60 may receive and process data from a single source or multiple sources.

The controller 30 further includes a navigation controller 62 for communicating the position data relating to the femur F, tibia T, and tool 20 to the manipulator controller 60. The manipulator controller 60 receives and processes the position data provided by the navigation controller 62 to direct movement of the manipulator 14. In one embodiment, as shown in FIG. 1, the navigation controller 62 is implemented on the navigation computer 36.

The manipulator controller 60 or navigation controller 62 may also communicate positions of the patient 12 and tool 20 to the operator by displaying an image of the femur F and/or tibia T and the tool 20 on the display 38. The manipulator computer 26 or navigation computer 36 may also display instructions or request information on the display 38 such that the operator may interact with the manipulator computer 26 for directing the manipulator 14.

As shown in FIG. 2, the controller 30 includes a boundary generator 66. The boundary generator 66 is a software module that may be implemented on the manipulator controller 60, as shown in FIG. 2. Alternatively, the boundary generator 66 may be implemented on other components, such as the navigation controller 62. As described in detail below, the boundary generator 66 generates the virtual boundaries for constraining the tool 20.

Figure 3:
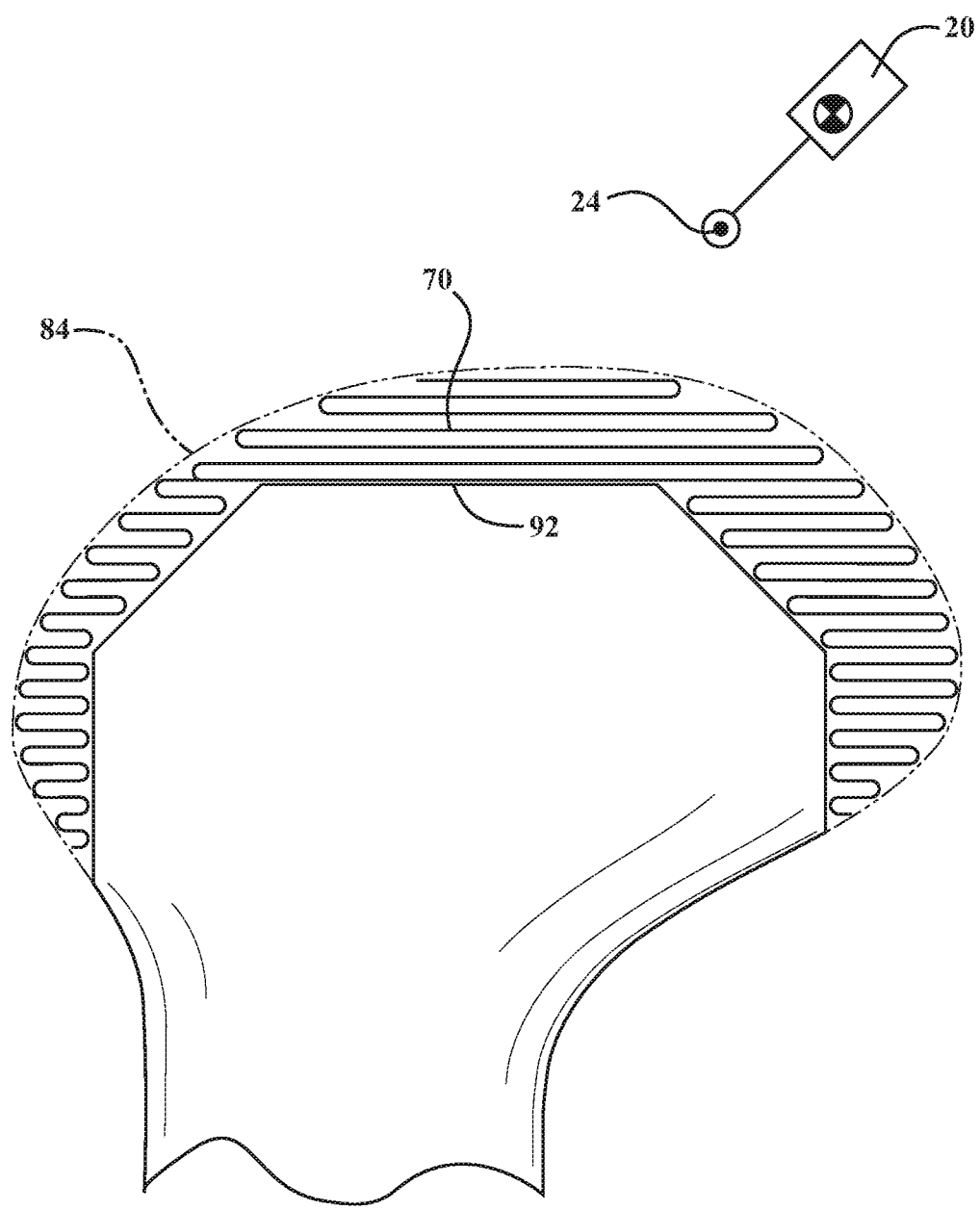
FIG. 3 illustrates the tool interacting with the anatomy along a tool path to form a target surface according to one embodiment of the invention.

A tool path generator 68 is another software module run by the controller 30, and more specifically, the manipulator controller 60. The tool path generator 68 generates a tool path 70 as shown in FIG. 3, which represents a bone, a section of which is to be removed to receive an implant. In FIG. 3, the tool path 70 is represented by the back and forth line. The smoothness and quality of the finished surface depends in part of the relative positioning of the back and forth line. More specifically, the closer together each back and forth pass of the line, the more precise and smooth is the finished surface. Dashed line 84 represents the perimeter of the bone that is to be removed using manipulator 14. One exemplary system and method for generating the tool path 70 is explained in U.S. Pat. No. 9,119,655, entitled, "Surgical Manipulator Capable of Controlling a Surgical Instrument in Multiple Modes," the disclosure of which is hereby incorporated by reference.

II. System and Method Overview

Figure 4:
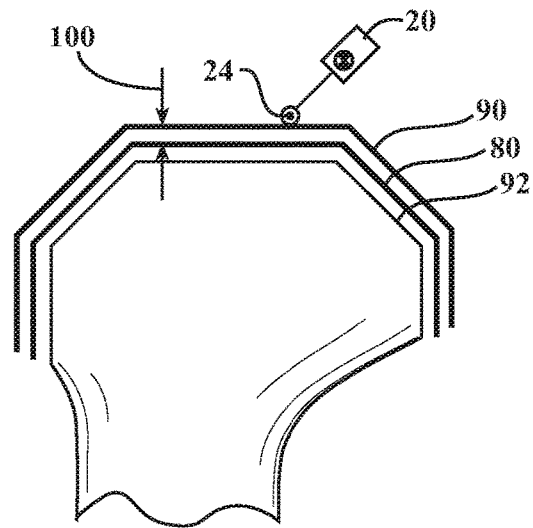
FIG. 4 illustrates operation of the system in a first mode wherein the tool in constrained in relation to an intermediate virtual boundary spaced with respect to a target virtual boundary.
Figure 5:
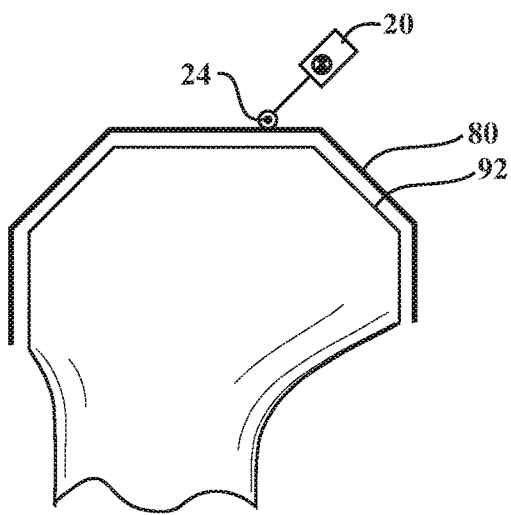
FIG. 5 illustrates operation of the system in a second mode wherein the tool in constrained in relation to the target virtual boundary that is offset from a target surface of the anatomy.

The system 10 and method for manipulating the anatomy with the tool 20 include defining with the controller 30, a first, or intermediate virtual boundary 90 and a second, or target virtual boundary 80 associated with the anatomy, as shown in FIGS. 4 and 5. The intermediate virtual boundary 90 is spaced apart from the target virtual boundary 80. The intermediate virtual boundary 90 is activated in a first mode as shown in FIG. 4. Movement of the tool 20 is constrained in relation to the intermediate virtual boundary 90 in the first mode. The intermediate virtual boundary 90 is deactivated in a second mode, as shown in FIG. 5. Movement of the tool 20 is constrained in relation to the target virtual boundary 80 in the second mode.

One exemplary system and method for generating the virtual boundaries 80, 90 is explained in U.S. Pat. No. 9,119,655, entitled, "Surgical Manipulator Capable of Controlling a Surgical Instrument in Multiple Modes," the disclosure of which is hereby incorporated by reference. The boundary generator 66 generates maps that define the target and intermediate virtual boundaries 80, 90. These boundaries 80, 90 delineate between tissue the tool 20 should remove and tissue the tool 20 should not remove. Alternatively, these boundaries 80, 90 delineate between tissue to which the tool 20 energy applicator 24 should be applied and tissue to which the energy applicator 24 should not be applied. As such, the target and intermediate virtual boundaries 80, 90 are cutting or manipulation boundaries, which limit movement of the tool 20. Often, but not always, the virtual boundaries 80, 90 are defined within the patient 12.

As shown throughout, the target and intermediate virtual boundaries 80, 90 independently constrain movement of the tool 20 between the first and second modes. That is, the tool 20 is constrained by either the intermediate virtual boundary 90 in the first mode or the target virtual boundary 80 in the second mode. Methods for constraining movement of the tool 20 are explained in U.S. Pat. No. 9,119,655, entitled, "Surgical Manipulator Capable of Controlling a Surgical Instrument in Multiple Modes," the disclosure of which is hereby incorporated by reference.

The surgical system 10 allows switching between the first and second modes to provide different constraint configurations for the tool 20. When the first mode is switched to the second mode, as shown in FIG. 5 the intermediate virtual boundary 90 is deactivated, leaving the target virtual boundary 80. Thus, in the second mode, the tool 20 is permitted to reach the target virtual boundary 80 because the intermediate virtual boundary 90 is not constraining the tool 20. The tool 20 is constrained in relation to the target virtual boundary 80 when the intermediate virtual boundary 90 is inactivated.

When the second mode is switched to the first mode, as shown in FIG. 4, the intermediate virtual boundary 90 is activated or re-activated. The tool 20 is constrained in relation to the intermediate virtual boundary 90 when the intermediate virtual boundary 90 is activated. Thus, in the first mode, the intermediate virtual boundary 90 prevents the tool 20 from reaching the target virtual boundary 80.

The manipulator 14 is configured to receive instructions from the controller 30 and move the tool 20 in relation to the intermediate virtual boundary 90 in the first mode and/or the target virtual boundary 80 in the second mode. The navigation system 32 tracks movement of the tool 20 in relation to the intermediate virtual boundary 90 in the first mode and/or the target virtual boundary 80 in the second mode. As the tool 20 moves, the manipulator 14 and navigation system 32 cooperate to determine if the tool 20 is inside the intermediate virtual boundary 90 in the first mode and/or the target virtual boundary 80 in the second mode. The manipulator 14 selectively limits the extent to which the tool 20 moves. Specifically, the controller 30 constrains the manipulator 14 from movement that would otherwise result in the application of the tool 20 outside of the intermediate virtual boundary 90 in the first mode and/or the target virtual boundary 80 in the second mode. If the operator applies forces and torques that would result in the advancement of the tool 20 beyond the intermediate virtual boundary 90 in the first mode and/or target virtual boundary 80 in the second mode, the manipulator 14 does not emulate this intended positioning of the tool 20.

As shown in FIG. 5, the target virtual boundary 80 is associated with the anatomy, and more specifically a target surface 92 of the anatomy. The target virtual boundary 80 is defined in relation to the target surface 92. Target surface 92 is also the outline of the bone remaining after the removal procedure and is the surface to which the implant is to be mounted. In other words, the target surface 92 is a contiguous defined surface area of the tissue that is to remain after cutting has completed.

As shown in FIG. 5, during the procedure, the target virtual boundary 80 may be slightly offset or spaced apart from the target surface 92. In one embodiment, this is done to account for the size and manipulation characteristics of the tool 20. The manipulation characteristics of the tool 20 may cause the tool 20 to breach the target virtual boundary 80. To account for this overreaching, the target virtual boundary 80 may be translated from target surfaces 82 by a predetermined distance defined between the target surface 92 and the target virtual boundary 80. In one example, the distance is equivalent to half of the thickness of the tool 20. In another embodiment, the target virtual boundary 80 may be slightly offset or spaced apart from the target surface 92 depending on how the tool 20 and energy applicator 24 are tracked. For example, the energy applicator 24 may be tracked based on points based on a center of the energy applicator 24 rather than points based on an exterior cutting surface of the energy applicator 24. In such instances, offsetting the target virtual boundary 80 from the target surface 92 provides accommodates the center tracking to prevent overshooting of the target surface 92. For instance, when the energy applicator of the tool 20 is a spherical bur, the target virtual boundary is offset by half the diameter of the bur when the tool center point (TCP) of the bur is being tracked. As a result, when the TCP is on the target virtual boundary 80, the outer surface of the bur is at the target surface 92.

The intermediate virtual boundary 90 is spaced apart from the target virtual boundary 80. As shown in FIG. 4, the intermediate virtual boundary 90 is spaced further from the target surface 92 than the target virtual boundary 80 is spaced from the target surface 92. In essence, the target virtual boundary 80 is located between the target surface 92 and the intermediate virtual boundary 90. Since the intermediate virtual boundary 90 is spaced further from the target surface 92, movement of the tool 20 is generally more restricted in relation to the intermediate virtual boundary 90 as compared in relation to the target virtual boundary 80. Said differently, movement of the tool 20 is more restricted in the first mode as compared with the second mode.

A zone 100 is defined between the target and intermediate virtual boundaries 80, 90, as shown in FIG. 4. The boundaries 80, 90 may be spaced according to any suitable distance. In one example, the target and intermediate virtual boundaries 80, 90 are spaced by approximately one half millimeter such that the zone 100 has a thickness of one half millimeter. In one sense, the intermediate virtual boundary 90 may be considered an offset boundary in relation to the target virtual boundary 80. In general, the controller 30 prevents the tool 20 from penetrating the zone 100 in the first mode. Preventing the tool 20 from penetrating the zone 100 in the first mode may occur regardless of whether or not the target virtual boundary 80 is active. The controller 30 allows the tool 20 to penetrate the zone 100 in the second mode. The zone 100) may be defined independent of whether the target and/or intermediate virtual boundaries 80, 90 are active or inactive.

The target and intermediate virtual boundaries 80, 90 may have the same profile has shown in FIG. 4. Specifically, the target and intermediate virtual boundaries 80, 90 have profiles that are similar to the target surface 92. Having similar profiles may be useful to promote gradual formation of the target surface 92.

Displays 38 may show representations of the target and intermediate virtual boundaries 80, 90 and the anatomy being treated. Additionally, information relating to the target and intermediate virtual boundaries 80, 90 may be forwarded to the manipulator controller 60 to guide the manipulator 14 and corresponding movement of the tool 20 relative to these virtual boundaries 80, 90 so that the tool 20 does not intrude on such.

The manipulator controller 60 may continuously track movement of the target and intermediate virtual boundaries 80, 90. In some instances, the anatomy may move from a first position to a second position during the procedure. In such instances, the manipulator controller 60 updates the position of the virtual boundaries 80, 90 consistent with the second position of the anatomy.

In one embodiment, the first mode and/or second mode is/are an autonomous mode or a manual mode. Examples of the autonomous mode and manual mode are described in U.S. Pat. No. 9,119,655, entitled, "Surgical Manipulator Capable of Controlling a Surgical Instrument in Multiple Modes," the disclosure of which is hereby incorporated by reference.

In one embodiment, in the first mode, the system 10 operates in the manual mode. The operator manually directs, and the manipulator 14 controls, movement of the tool 20 and, in turn, the energy applicator 24 at the surgical site. The operator physically contacts the tool 20 to cause movement of the tool 20. The manipulator 14 monitors the forces and torques placed on the tool 20 by the operator in order to position the tool 20. These forces and torques are measured by a sensor that is part of the manipulator 14. In response to the applied forces and torques, the manipulator 14 mechanically moves the tool 20 in a manner that emulates the movement that would have occurred based on the forces and torques applied by the operator. Movement of the tool 20 in the first mode is constrained in relation to the intermediate virtual boundary 90. In this case, the intermediate virtual boundary 90 acts as a haptic boundary and the manipulator 14 provides the operator with haptic feedback to indicate the location of the intermediate virtual boundary 90 to the operator. For instance, by virtue of the manipulator 14 preventing or resisting movement of the tool 20 beyond the intermediate virtual boundary 90, the operator haptically senses a virtual wall when reaching the intermediate virtual boundary 90.

At any time during manual manipulation in the first mode, or after manipulation in the first mode is complete, the system 10 allows switching from the first mode to the second mode. In one embodiment, switching between the first and second modes occurs in response to manual input. For example, the operator may use some form of control to manage remotely which of the first and second modes should be active. Alternatively, switching may be implemented autonomously in response to certain events or conditions. For example, the system 10 may determine that the requisite amount of tissue has been removed in the first mode and switch to the second mode in response. Those skilled in the art appreciate that switching between first and second modes may be performed according to other methods not explicitly described herein.

In the second mode, in one embodiment, the manipulator 14 directs autonomous movement of the tool 20 and, in turn, the energy applicator 24 at the surgical site. The manipulator 14 is capable of moving the tool 20 free of operator assistance. Free of operator assistance may mean that an operator does not physically contact the tool 20 to apply force to move the tool 20. Instead, the operator may use some form of control to remotely manage starting and stopping of movement. For example, the operator may hold down a button of a remote control to start movement of the tool 20 and release the button to stop movement of the tool 20. Alternatively, the operator may press a button to start movement of the tool 20 and press a button to stop movement of the tool 20. Movement of the tool 20 in the second mode is constrained in relation to the target virtual boundary 80.

The system 10 and method advantageously provide the opportunity to selectively control activation of the intermediate virtual boundary 90 between the first and second modes. By doing so, the system 10 and method provide different virtual boundary configurations for each of the first and second modes. This increases versatility of the surgical system and performance of the operator. In some embodiments, this advantageously provides the opportunity for the operator to use the manipulator 14 in a bulk-manipulation fashion in the first mode. The operator may initially operate the tool 20 manually in order to remove a large mass of tissue. This part of the procedure is sometimes referred to as debulking. The operator, knowing that the intermediate virtual boundary 90 is constraining the tool 20 away from the target surface 92, may take measures to perform bulk-manipulation that is much faster than otherwise possible during autonomous manipulation. Once the bulk of the tissue is removed manually, the system 10 may be switched to the second mode to provide autonomous manipulation of the remaining portion of the tissue in a highly accurate and controlled manner. Said differently, in the second mode, the operator may require fine positioning of the instrument to define the surfaces of the remaining tissue. This part of the procedure is sometimes known as the finishing cut, and is possible because the intermediate virtual boundary 90 is inactive and the target virtual boundary 80 is active.

III. Other Embodiments

The target and virtual boundaries 80, 90 may be derived from various inputs to the manipulator 14, and more specifically, the boundary generator 66. One input into the boundary generator 66 includes preoperative images of the site on which the procedure is to be performed. If the manipulator 14 selectively removes tissue so the patient 12 may be fitted with an implant, a second input into the boundary generator 66 is a map of the shape of the implant. The initial version of this map may come from an implant database. The shape of the implant defines the boundaries of the tissue that should be removed to receive the implant. This relationship is especially true if the implant is an orthopedic implant intended to be fitted to the bone of the patient 12.

Another input into boundary generator 66 is the operator settings. These settings may indicate to which tissue the energy applicator 24 should be applied. If the energy applicator 24 removes tissues, the settings may identify the boundaries between the tissue to be removed and the tissue that remains after application of the energy applicator 24. If the manipulator 14 assists in the fitting of an orthopedic implant, these settings may define where over the tissue the implant should be positioned. These settings may be entered preoperatively using a data processing unit. Alternatively, these settings may be entered through an input/output unit associated with one of the components of the system 10 such as with navigation interface 40, 42.

Based on the above input data and instructions, boundary generator 66 may generate the target and intermediate virtual boundaries 80, 90. The boundaries 80, 90 may be two-dimensional or three-dimensional. For example, the target and intermediate virtual boundaries 80, 90 may be generated as a virtual map or other three-dimensional model, as shown in the Figures. The created maps or models guide movement of the tool 20. The models may be displayed on displays 38 to show the locations of the objects. Additionally, information relating to the models may be forwarded to the manipulator controller 60 to guide the manipulator 14 and corresponding movement of the tool 20 relative to the target and intermediate virtual boundaries 80, 90.

In practice, prior to the start of the procedure the operator at the surgical site may set an initial version of the virtual target and intermediate virtual boundaries 80, 90. At the start of the procedure, data that more precisely defines the implant that is to be actually fitted to the patient 12 may be loaded into the boundary generator 66. Such data may come from a storage device associated with the implant such as a memory stick or an RFID tag. Such data may be a component of the implant database data supplied to the boundary generator 66. These data are based on post manufacture measurements of the specific implant. These data provide a definition of the shape of the specific implant that, due to manufacturing variations, may be slightly different than the previously available stock definition of implant shape. Based on this implant-specific data, the boundary generator 66 may update the target and intermediate virtual boundaries 80, 90 to reflect the boundaries between the tissue to be removed and the tissue that should remain in place. Implants that could be implanted into the patient 12 include those shown in U.S. patent application Ser. No. 13/530,927, filed on Jun. 22, 2012 and entitled, "Prosthetic Implant and Method of Implantation", hereby incorporated by reference. The implants disclosed herein could be implanted in the patient 12 after the appropriate amount of material, such as bone, is removed. Other implants are also contemplated.

In one embodiment, the target virtual boundary 80 is derived from points in a coordinate system associated with the anatomy. The target virtual boundary 80 may be interpolated by connecting each of the captured points together. This creates a web or mesh that defines the target virtual boundary 80. If only two points are captured, the target virtual boundary 80 may be a line between the points. If three points are captured, the target virtual boundary 80 may be formed by lines connecting adjacent points. The displays 38 may provide visual feedback of the shape of the target virtual boundary 80 created. The input devices 40, 42 may be utilized to control and modify the target virtual boundary 80 such as by shifting the boundary, enlarging or shrinking the boundary, changing the shape of the target virtual boundary 80, etc. Those skilled in the art understand that the target virtual boundary 80 may be created according to other methods not specifically described herein.

Figure 7:
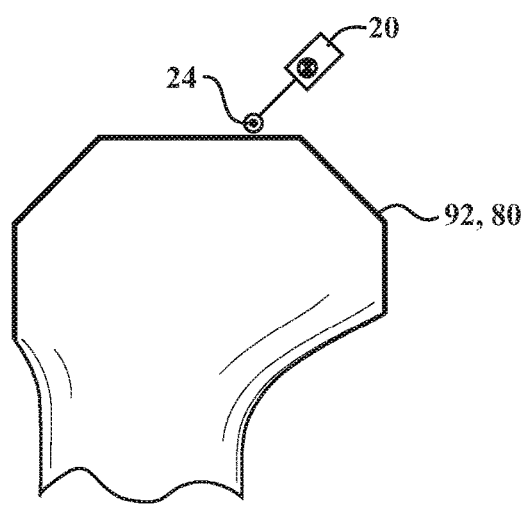
FIG. 7 illustrates operation of the system in the second mode wherein the tool in constrained in relation to the target virtual boundary aligned with the target surface of the anatomy.
Figure 10:
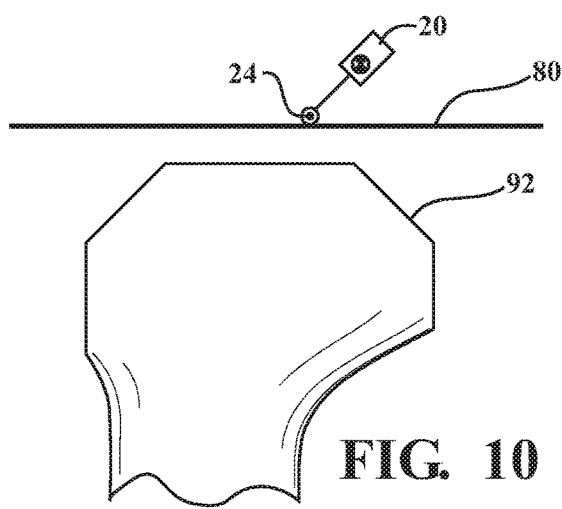
FIG. 10 illustrates operation of the system in the second mode wherein the tool in constrained in relation to the target virtual boundary having a profile different than the target surface.

Alternative arrangements and configurations of the target virtual boundary 80 are shown in FIGS. 7 and 10. In some instances, as shown in FIG. 7, it may be suitable to align the target virtual boundary 80 directly with the target surface 92 of the anatomy rather than to have an offset between the two. For example, the manipulation characteristics of the tool 20 may not extend beyond the target virtual boundary 80. Additionally or alternatively, the tool 20 may be tracked based on points that are on an exterior surface of the energy applicator 24 rather than points that are in the center of the energy applicator 24. In such instances, aligning the target virtual boundary 80 with the target surface 92 provides accurate manipulation to create the target surface 92. In yet another embodiment, the tool 20 may be tracked based on an envelope outlining a range of movement of the exterior surface of the tool 20. For instance, when the tool 20 is a saw blade, the envelope encompasses the range of movement of the exterior surface of the saw blade such that movement of the exterior surface of the saw blade during oscillations of the saw blade is captured within the envelope. Positioning of the target virtual boundary 80 may take into account the envelope.

In other examples, as shown in FIG. 5, the target virtual boundary 80 is generally un-aligned with the target surface 92. Instead, the target virtual boundary 80 is spaced apart from and rests beyond the target surface 92. Those skilled in the art appreciate that the target virtual boundary 80 may have other configurations not specifically recited herein.

The intermediate virtual boundary 90 may be formed in a similar manner as the target virtual boundary 80. Alternatively, the controller 30 may derive the intermediate virtual boundary 90 from the target virtual boundary 80. For example, the controller 30 may copy the target virtual boundary 80 to form the intermediate virtual boundary 90. The copy of the target virtual boundary 80 may be modified or transformed according to any suitable method to form the intermediate virtual boundary 90. For example, the copy of the target virtual boundary 80 may be translated, shifted, skewed, resized, rotated, reflected, and the like. Those skilled in the art understand that the intermediate virtual boundary 90 may be derived from the target virtual boundary 80 according to other methods not specifically described herein.

Figure 9:
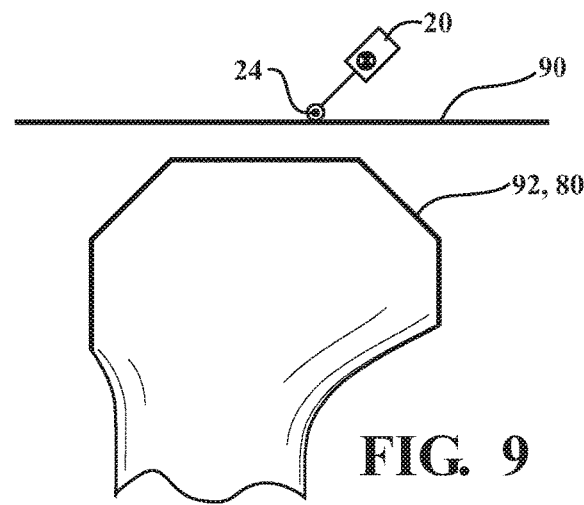
FIG. 9 illustrates operation of the system in the first mode wherein the tool in constrained in relation to the intermediate virtual boundary having a profile different than the target virtual boundary.

The target virtual boundary 80 and the intermediate virtual boundary 90 may have any suitable profile. For example, as shown in FIG. 5, the target virtual boundary 80 has a profile that is similar to the profile of the target surface 92. In FIG. 10, the target virtual boundary 80 has a profile that is planar or flat. In FIG. 4, the intermediate virtual boundary 90 has a profile that is similar to the profile of the target surface 92. In FIG. 9, the intermediate virtual boundary 90 has a profile that is planar or flat. Those skilled in the art appreciate that the target virtual boundary 80 and the intermediate virtual boundary 90 may have other profiles not specifically recited herein.

The target and intermediate virtual boundaries 80, 90 need not have the same profile, as shown in FIG. 4. Instead, the boundaries 80, 90 may have the different profiles with respect to one another, as shown in FIG. 9. In FIG. 9, the profile of the target virtual boundary 80 is similar to the profile of the target surface 92 whereas the profile of the intermediate virtual boundary 90 is planar. Of course, those skilled in the art appreciate that either profile of the boundaries 80, 90 may differ from those illustrated in FIG. 9. The profiles of each of the boundaries 80, 90 may be generated manually or automatically in accordance with any suitable technique. Having different profiles may be useful depending on several factors, including, but not limited to, the tool 20 and/or mode being used.

Figure 6:
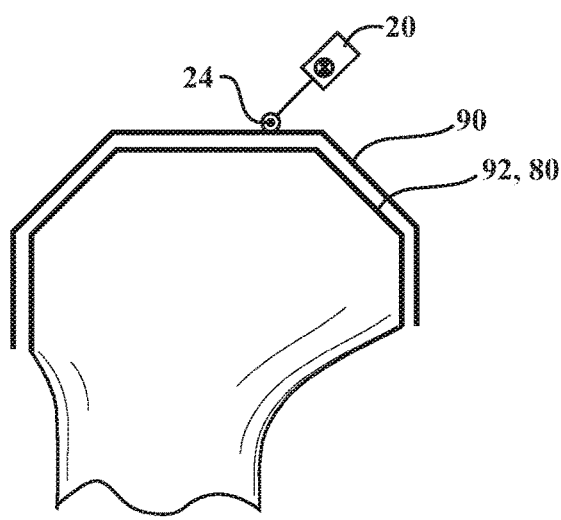
FIG. 6 illustrates operation of the system in the first mode wherein the tool in constrained in relation to the intermediate virtual boundary and wherein the target virtual boundary remains activated.
Figure 8:
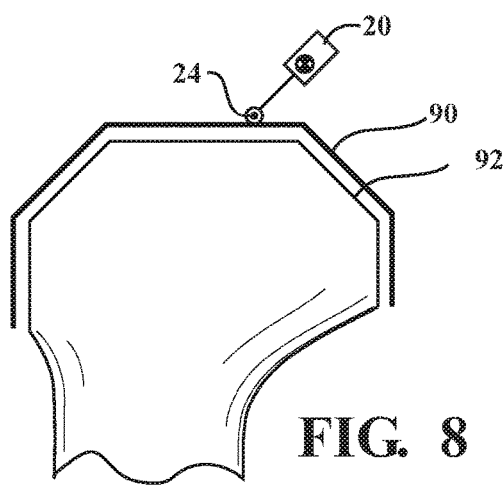
FIG. 8 illustrates operation of the system in the first mode wherein the tool in constrained in relation to the intermediate virtual boundary and wherein the target virtual boundary is deactivated.

Several different embodiments are possible for the target virtual boundary 80 in view of the first mode. As described, in the first mode, the intermediate virtual boundary 90 is active and the tool 20 is constrained in relation to the intermediate virtual boundary 90. However, activation and deactivation of the target virtual boundary 80 may be controlled in the first mode. For example, as shown in FIGS. 4, 6, and 9, the target virtual boundary 80 may be activated in the first mode simultaneously while the intermediate boundary 90 is active. In one example, this may be done for redundancy purposes. As described, the intermediate boundary 90 is an important feature of the system 10 because it operates as a cutting boundary. Any errors in implementation of the intermediate boundary 90 may, in turn, leave the target surface 92 exposed to error. By simultaneously activating the target virtual boundary 80, the system 10 increases reliability by having the target virtual boundary 80 as a back up to the intermediate virtual boundary 90. This may also allow the manipulator 14 to operate at higher speeds knowing that the target virtual boundary 80 is provided as a redundancy. Alternatively, as shown in FIG. 8, the target virtual boundary 80 may be deactivated in the first mode. This may be done to preserve computing resources, reduce complexity in implementation, and the like.

Control of the target virtual boundary 80 in the first mode may be automatic or manual. For example, the operator may manually activate or deactivate the target virtual boundary 80 in the first mode. Alternatively, the system 10 may automatically determine whether it is appropriate to activate the target virtual boundary 80 depending on certain events or conditions. For example, detection of instability of the system 10 may trigger automatic activation of the target virtual boundary 80 in the first mode.

The first mode and the second mode may be different type (i.e., manual/autonomous) or the same type depending on the application and a variety of other factors. One such factor is duration of the operating procedure, which is largely affected by a feed rate of the tool 20. The feed rate is the velocity at which a distal end of the energy applicator 24 advances along a path segment. In general, in the autonomous mode, the manipulator 14 may be more accurate but provides a slower feed rate than in the manual mode. In the manual mode, the manipulator 14 may be less accurate but is capable of providing a faster feed rate than in the autonomous mode. This trade-off between accuracy and feed rate is one factor dictating what type of control is implemented during the first and second modes.

A frequency of back-and-forth oscillations of the tool 20 along the cutting path 70 may differ between the first and second modes. Generally, the greater the frequency of the oscillations, the closer together the cutting path 70 oscillations and the "finer" the cut provided by the tool 20. On the other hand, the lesser the frequency of the oscillations, the more spaced apart the cutting path 70 oscillations and the "bulkier" the cut provided by the tool 20.

Generally, as the tool 20 traverses the cutting path 70, the tool 20 forms ribs 110 in the anatomy (distal femur), as shown in FIGS. 13 and 14. Examples of such ribs are shown in U.S. patent application Ser. No. 14/195,113, entitled, "Bone Pads," the disclosure of which is hereby incorporated by reference. The specific three-dimensional geometry of the ribs 110 is the result of a rotational cutting tool, such as a burr for example, making a plurality of channeled preparations 112. In the embodiments shown, the plurality of channeled preparations 112 follow a substantially linear path resulting from back and forth movement of the tool 20 along the cutting path 70. The ribs 110 have a height 114, a width 116 and a plurality of protrusions 118. When the first and second modes exhibit different cutting path 70 oscillation frequencies, the first and second modes produce ribs 110 having different configurations.

Figure 13A:
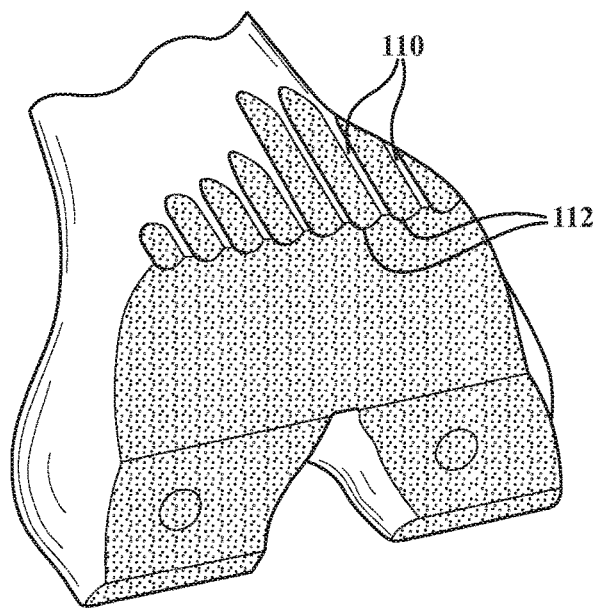
FIGS. 13A-13C illustrate characteristics of the anatomy resulting after bulk cutting in the first mode, according to one example.
Figure 13B:
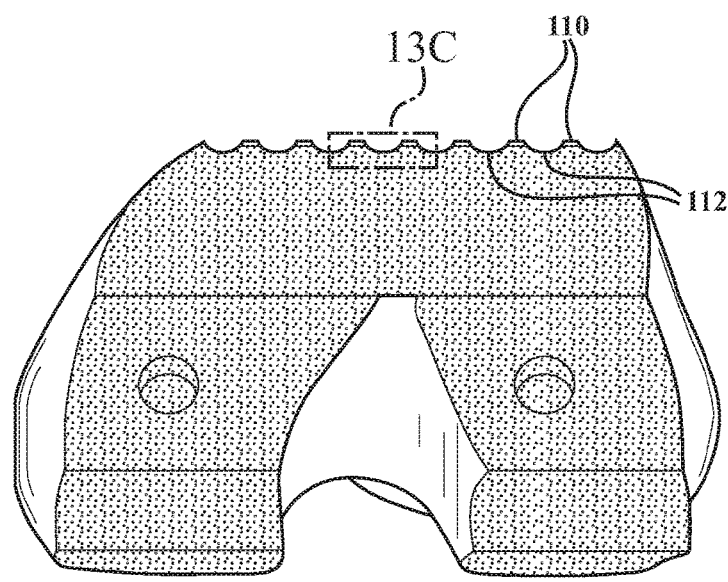
Figure 13C:
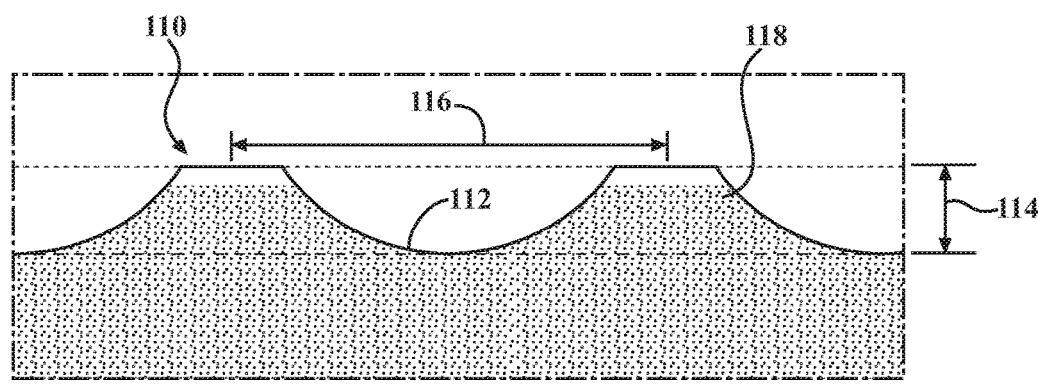
Figure 14A:
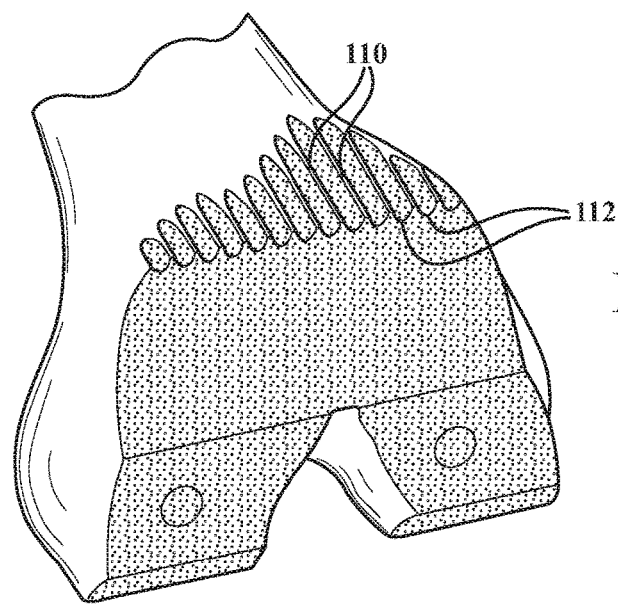
FIGS. 14A-14C illustrate characteristics of the anatomy resulting after fine cutting in the second mode, according to one example.
Figure 14B:
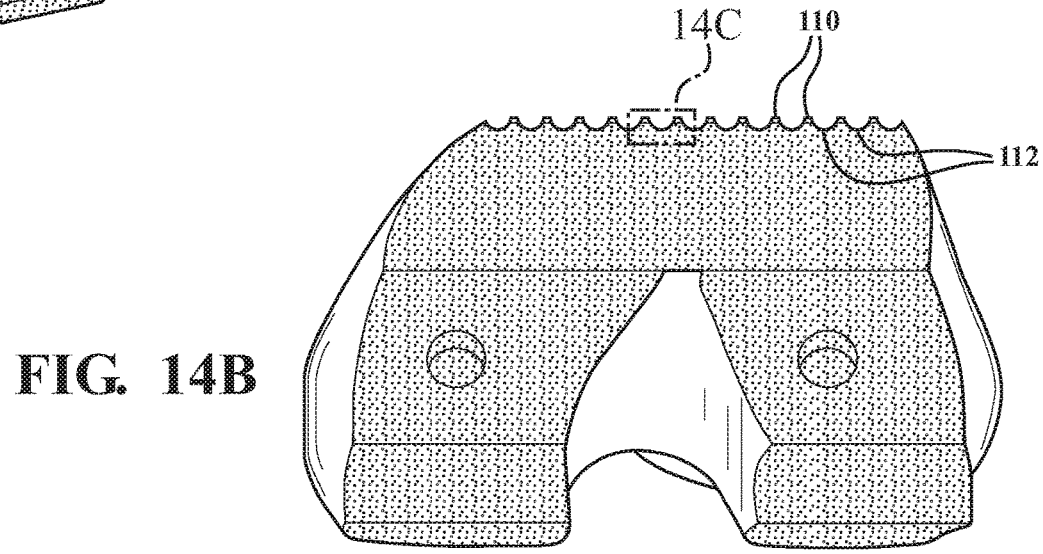
Figure 14C:
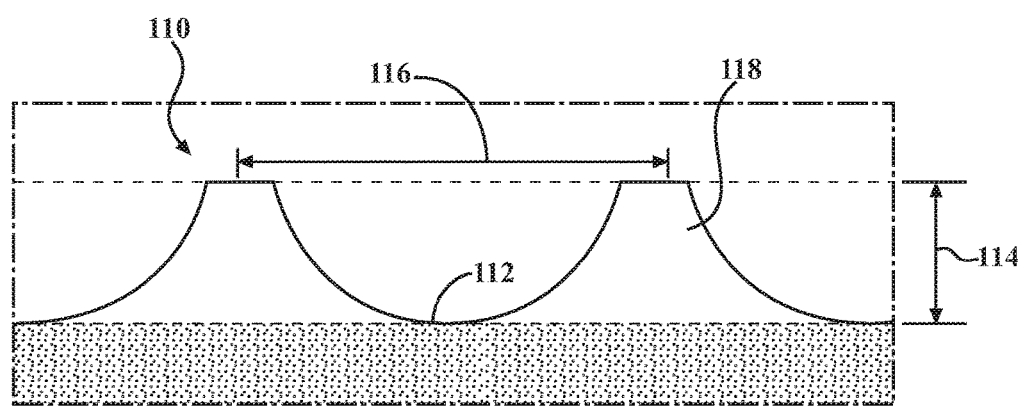

In one example, the oscillations are more frequent in the second mode than the first mode. For example, FIGS. 13A-C illustrate ribs 110 resulting from bulk-cutting in the first mode and FIGS. 14A-C illustrate ribs 110 resulting from fine-cutting in the second mode. Consequently, the ribs 110 are formed differently between the first and second modes. Specifically, the ribs 110 formed in the first mode (FIG. 13B) exhibit a larger peak-to-peak distance between adjacent ribs 110 as compared with ribs 110 formed in the second mode (FIG. 14B), which are closer together. The height and/or width of the ribs 110 may also be different between the first and second modes. For example, the width 116 of the ribs 110 in the bulk-cutting mode (FIG. 13C) is greater than the width 116 of the ribs 110 in the fine-cutting mode (FIG. 14C). Conversely, the height 114 of the ribs 110 in the bulk-cutting mode (FIG. 13C) is less than the height 114 of the ribs 110 in the fine-cutting mode (FIG. 14C). Additionally, the geometry of the protrusions 118 formed in the first mode may differ from those formed in the second mode. The first and second modes advantageously provide different surface finishes appropriate for the specific application. Those skilled in the art recognize that the first and second modes may cause differences in characteristics of the anatomy other than those described herein with respect to the ribs.

In one embodiment, the first mode is the autonomous mode and the second mode is the manual mode. Movement of the tool 20 occurs autonomously in the first mode and is constrained in relation to the intermediate virtual boundary 90. Autonomous manipulation in the first mode is switched to manual manipulation in the second mode. Movement of the tool 20 occurs manually in the second mode and is constrained in relation to the target virtual boundary 80. Specifically, the operator may rely on the surgical system 10 to perform a majority of the manipulation of the tissue autonomously in the first mode. As needed, the operator may switch to manual manipulation in the second mode to interface directly with the target virtual boundary 80, which is closer to the target surface 92. By doing so, the operator can perform versatile procedures, such as creating irregular surface finishes on the target surface 92. The system 10 and method allow the operator to make final cuts in the target surface 92 that secure the implant better than may be planned with autonomous manipulation. Moreover, operators may prefer not to allow the system 10 to autonomously cut tissue entirely up to the target surface 92. Having the intermediate virtual boundary 90 activated in the first mode provides added comfort for operators during autonomous manipulation because the intermediate virtual boundary 90 is spaced from the target virtual boundary 80.

In another embodiment, the first mode and the second mode are both manual modes. Movement of the tool 20 occurs manually in the first mode and is constrained in relation to the intermediate virtual boundary 90. Manual manipulation in the first mode is switched to manual manipulation in the second mode. Although manual manipulation is preserved in the second mode, the boundary configuration changes because the intermediate virtual boundary 90 is deactivated. In the second mode, movement of the tool 20 occurs manually and is constrained in relation to the target virtual boundary 80. This embodiment advantageously provides the opportunity for the operator to use the manipulator 14 in a bulk-manipulation fashion in both the first and second modes. The operator, knowing that the intermediate virtual boundary 90 is constraining the tool 20 away from the target surface 92, may take measures to perform bulk manipulation that is much faster and more aggressive than otherwise possible during autonomous manipulation. Once the bulk of the tissue is removed manually in the first mode, the system 10 may be switched to the second mode for allowing manual manipulation of the remaining portion of the tissue. In the second mode, the operator may manually create irregular or fine surface finishes on the target surface 92 in relation to the target virtual boundary 80.

In yet embodiment, the first mode and the second mode are both autonomous modes. Movement of the tool 20 occurs autonomously in the first mode and is constrained in relation to the intermediate virtual boundary 90. Autonomous manipulation in the first mode is switched to autonomous manipulation in the second mode. Although switching to the second mode maintains autonomous manipulation, the boundary configuration changes by deactivating the intermediate virtual boundary 90. In the second mode, movement of the tool 20 occurs autonomously and is constrained in relation to the target virtual boundary 80. This embodiment advantageously provides the opportunity to manipulate the tissue autonomously in a highly accurate and controlled manner throughout the first and second modes. Additionally, the operator may examine the tissue after autonomous manipulation in the first mode. In other words, rather than having the surgical device 10 autonomously manipulate the tissue entirely up to the target surface 92, the first mode may be used as a first-phase whereby the operator checks the progress and accuracy of the autonomous cutting before deactivating the intermediate virtual boundary 90 in the second mode.

In one embodiment, the system and method implement "n" modes. For example, the system and method may implement three or more modes. The first mode may be a manual mode. The second mode may be an autonomous mode exhibiting autonomous bulk-cutting, as shown in FIG. 13, for example. The third mode may be an autonomous mode exhibiting autonomous fine-cutting, as shown in FIG. 14, for example. Those skilled in the art appreciate that any of the "n" modes may be a mode other than an autonomous or manual mode described herein.

Figure 15:
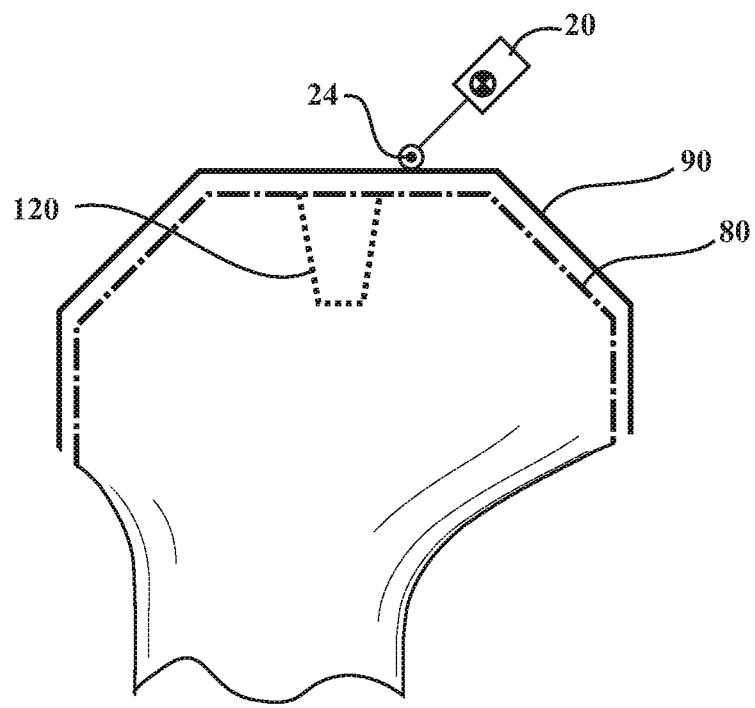
FIG. 15 illustrates operation of the system using three virtual boundaries each activated in a separate mode.

The system and method may implement "n" virtual boundaries. For example, the system and method may implement three or more virtual boundaries. The "n" virtual boundaries may be implemented for the "n" modes. One example of a three-virtual boundary implementation is illustrated in FIG. 15. In FIG. 15, the first virtual boundary 90, the second virtual boundary 80, and a third virtual boundary 120 are associated with the anatomy. Here, first virtual boundary 90 is provided to promote removal of cartilage and a superficial layer of bone, the second virtual boundary 80 is provided to promote removal of a deeper layer of bone for placement of an implant, and the third virtual boundary 120 is provided to promote formation of a hole in preparation for insertion of a peg/tail to secure the implant. The first virtual boundary 90 is activated in the first mode. Movement of the tool is constrained in relation to the first virtual boundary 90 in the first mode. The first virtual boundary 90 is deactivated in the second mode. The third virtual boundary 120 may remain active in the second mode. Movement of the tool is constrained in relation to the second virtual boundary 80 in the second mode. The second virtual boundary 80 is deactivated in a third mode. Movement of the tool is constrained in relation to the third virtual boundary 120 in the third mode.

In some embodiments, the "n" virtual boundaries are tissue specific. That is, the virtual boundaries are configured to constrain the tool 20 in relation to different types of tissue. For example, the "n" virtual boundaries may constrain the tool 20 in relation to soft tissue, cartilage, bone, ligaments, and the like. This may be done to protect the specific tissue from manipulation by the tool 20.

Additionally or alternatively, the "n" virtual boundaries are area/location specific. That is, the virtual boundaries are configured to constrain the tool 20 in relation to different areas or locations. For example, the "n" virtual boundaries may constrain the tool 20 in relation to other objects at the surgical site, such as retractors, other tools, trackers, and the like. Additionally, any one of the "n" virtual boundaries may serve as an irrigation boundary preventing the tool 20 from accessing a wet location in which the anatomy is undergoing irrigation. Those skilled in the art recognize that the "n" virtual boundaries and "n" modes may be implemented according to various other techniques not specifically recited herein.

Figure 16:
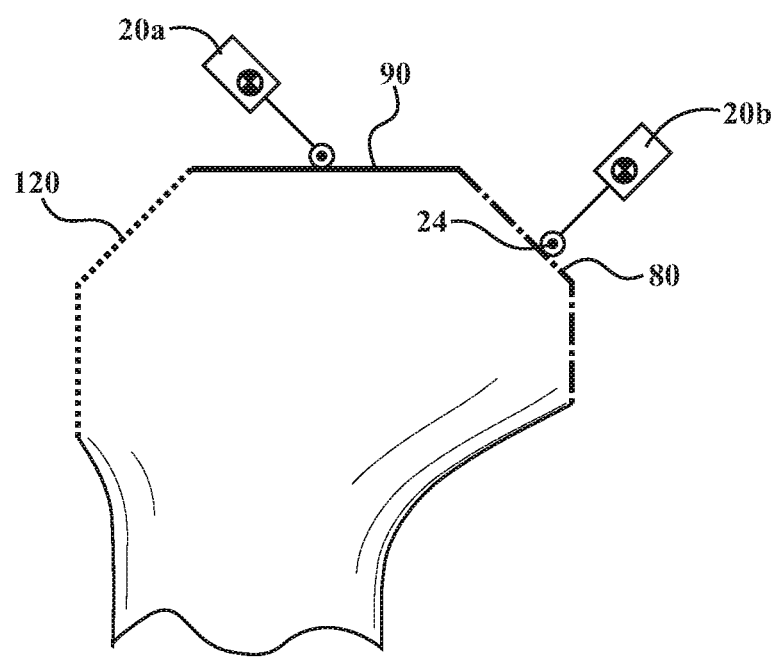
FIG. 16 illustrates operation of the system using more than one tool and three virtual boundaries that are simultaneously activated.

In other embodiments, the "n" virtual boundaries may be used in conjunction with more than one surgical tool 20. For example, as shown in FIG. 16, a first surgical tool 20*a* and a second surgical tool 20*b* are provided. The tools 20*a*, 20*b* move in a coordinated and/or synchronized fashion. The first virtual boundary 90 is defined with relation to an upper surface of the anatomy and the second and third virtual boundaries 80, 120 are defined along respective right and left surfaces of the anatomy. Here, the virtual boundaries 80, 90, 120 may be simultaneously active. Moreover, the virtual boundaries 80, 90, 120 may intersect, or touch, one another. In other examples, one tool 20 is used for manipulation while another tool is used for tissue retraction. In such instances, one virtual boundary may function as a manipulation constraining boundary while another virtual boundary functions as a tissue retraction boundary to prevent the retraction tool from leaving the intended area of retraction.

Any of the "n" virtual boundaries may be defined with respect to the anatomy such that virtual boundaries move as the anatomy position changes. This may be accomplished using the navigation and control techniques described herein.

The "n" virtual boundaries may be defined with respect to the same anatomy, as shown throughout the Figures, for example. In such instances, each of the "n" virtual boundaries follows the anatomy as the anatomy moves. Alternatively, the "n" virtual boundaries may be defined with respect to the different anatomy. For example, some "n" virtual boundaries may be defined with respect to the femur while other "n" virtual boundaries are defined with respect to the tibia. This may be done to protect the tibia from inadvertent manipulation. In such instances, spacing between the virtual boundaries may vary depending upon respective movement between the femur and tibia.

The controller 30 detects when the first mode is switched to the second mode, and vice-versa. The controller 30 may produce an alert to the operator to inform the operator whether constraint of the tool 20 is occurring in relation to the target virtual boundary 80 or intermediate virtual boundary 90. The alert may be visual, haptic, audible, and the like. Those skilled in the art recognize that the alert may be implemented according to various other ways not specifically described herein.

Figure 11:
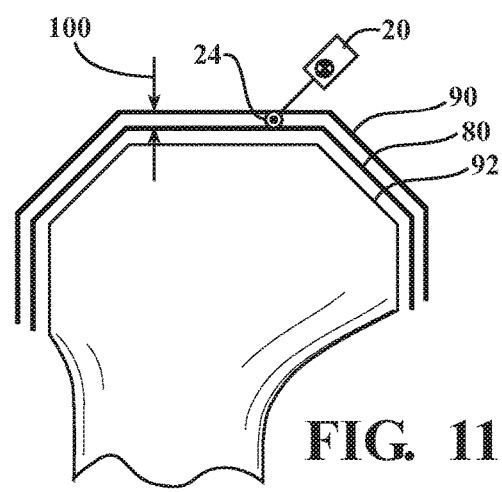
FIG. 11 illustrates operation of the system in the first mode wherein the tool is constrained between the intermediate and target virtual boundaries.
Figure 12:
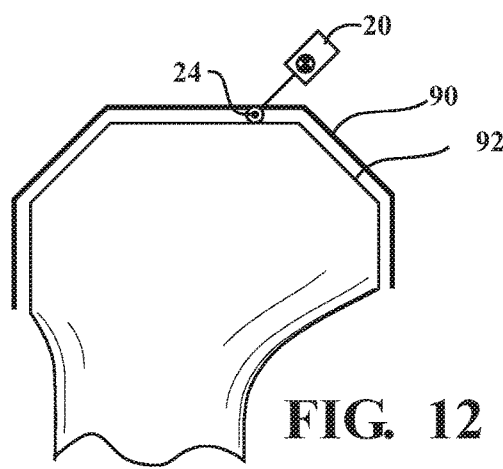
FIG. 12 illustrates operation of the system in the first mode wherein the tool is constrained between the intermediate virtual boundary and the target surface.

In some instances, the tool 20 may be within the zone 100 in the second mode at a moment when the system 10 is switched to the first mode. In such instances, the tool 20 may become trapped between the intermediate virtual boundary 90 and the target virtual boundary 80 or target surface 92. In one example, as shown in FIG. 11, the target virtual boundary 80 remains active in the first mode such that the tool 20 is trapped between the intermediate virtual boundary 90 and the target virtual boundary 80. In another example, as shown in FIG. 12, the target virtual boundary 80 is deactivated in the first mode such that the tool 20 is trapped between the intermediate virtual boundary 90 and the target surface 92.

Trapping the tool 20 in this manner may be deliberate or unintentional. When unintentional, the controller 30 may evaluate the position of the tool 20 when the second mode is switched to the first mode to prevent trapping the tool 20. For example, if the tool 20 is in the zone 100 at the time of switching to the first mode, the controller 30 may instruct the manipulator 14 to withdraw the tool 20 from the zone 100 such that the tool 20 is pulled beyond the intermediate virtual boundary 90. This may entail temporarily deactivating the intermediate virtual boundary 90 to allow exit of the tool 20. In other instances, it may be intended to trap the tool 20 within the zone 100 in the first mode. Trapping the tool 20 may be done to use the intermediate virtual boundary 90 as an upper constraining or cutting boundary. To illustrate, in the second mode, the tool 20 may penetrate tissue in the zone 100 with a narrow incision. Thereafter, the first mode may be re-activated to trap the tool 20 within the zone 100 with the intermediate virtual boundary 90. The operator may then remove tissue in the zone 100 manually or autonomously knowing that the tool 20 is constrained from above. This configuration may be useful for creating burrows in the tissue, and the like.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A system comprising:
a robotic manipulator comprising an arm;
an end effector coupled to the arm and being moveable by the arm for interacting with a target site in a manual mode and an autonomous mode of operation;
a navigation system configured to track a position of the end effector and the target site; and
one or more controllers configured to:
define a first virtual boundary relative to the target site,
prevent the end effector from penetrating the first virtual boundary in the manual mode; and
allow the end effector to penetrate the first virtual boundary in the autonomous mode.

2. The system of claim 1, wherein the one or more controllers are further configured to:
define a second virtual boundary relative to the target site, the first virtual boundary being spaced further apart from the target site than the second virtual boundary;
define a zone between the first and second virtual boundaries;
prevent the end effector from penetrating the zone in the manual mode; and
allow the end effector to penetrate the zone in the autonomous mode.

3. The system of claim 2, wherein the one or more controllers are further configured to evaluate the tracked position of the end effector relative to the zone.

4. The system of claim 3, wherein the one or more controllers are further configured to prevent movement of the end effector in the manual mode in response to determining that the position of the end effector is within the zone.

5. The system of claim 3, wherein the one or more controllers are further configured to allow movement of the end effector in the manual mode in response to determining that the position of the end effector is outside of the zone.

6. The system of claim 3, wherein the one or more controllers are further configured to:
control the robotic manipulator according to a first speed in response to determining that the position of the end effector is outside of the zone; and
control the robotic manipulator according to a second speed that is different from the first speed in response to determining that the position of the end effector is within the zone.

7. The system of claim 2, wherein the one or more controllers prevent the end effector from penetrating the zone in the manual mode by further being configured to control the robotic manipulator to prevent or resist attempted movement of the end effector beyond the first virtual boundary.

8. The system of claim 2, wherein the one or more controllers allow the end effector to penetrate the zone in the autonomous mode by further being configured to deactivate the first virtual boundary.

9. The system of claim 1, wherein the one or more controllers are configured to control a feed rate of the end effector such that the feed rate of the end effector in the autonomous mode is slower than the feed rate in the manual mode.

10. The system of claim 1, further comprising a sensor coupled to the end effector for monitoring forces and torques applied to the end effector.

11. A method of operating a system, the system comprising a robotic manipulator including an arm, an end effector coupled to the arm and being moveable by the arm for interacting with a target site in a manual mode and an autonomous mode of operation, a navigation system configured to track a position of the end effector and the target site, and one or more controllers for performing the steps of:
defining a first virtual boundary relative to the target site;
preventing the end effector from penetrating the first virtual boundary in the manual mode; and
allowing the end effector to penetrate the first virtual boundary in the autonomous mode.

12. The method of claim 11, further comprising the one or more controllers:
defining a second virtual boundary relative to the target site, the first virtual boundary being spaced further apart from the target site than the second virtual boundary;
defining a zone between the first and second virtual boundaries;
preventing the end effector from penetrating the zone in the manual mode; and
allowing the end effector to penetrate the zone in the autonomous mode.

13. The method of claim 12, further comprising the one or more controllers evaluating the tracked position of the end effector relative to the zone.

14. The method of claim 13, further comprising the one or more controllers preventing movement of the end effector in the manual mode in response to determining that the position of the end effector is within the zone.

15. The method of claim 13, further comprising the one or more controllers allowing movement of the end effector in the manual mode in response to determining that the position of the end effector is outside of the zone.

16. The method of claim 13, further comprising the one or more controllers:

controlling the robotic manipulator according to a first speed in response to determining that the position of the end effector is outside of the zone; and controlling the robotic manipulator according to a second speed that is different from the first speed in response to determining that the position of the end effector is within the zone.

17. The method of claim 12, wherein preventing the end effector from penetrating the zone in the manual mode further comprises the one or more controllers controlling the robotic manipulator to prevent or resist attempted movement of the end effector beyond the first virtual boundary.

18. The method of claim 12, wherein allowing the end effector to penetrate the zone in the autonomous mode further comprises the one or more controllers deactivating the first virtual boundary.

19. The method of claim 11, further comprising the one or more controllers controlling a feed rate of the end effector such that the feed rate of the end effector in the autonomous mode is slower than the feed rate in the manual mode.

20. The method of claim 11, further comprising the one or more controllers monitoring forces and torques applied to the end effector.

* * * * *